United States Patent
Amorelli et al.

(10) Patent No.: US 9,453,182 B1
(45) Date of Patent: Sep. 27, 2016

(54) DIMETHYLCYCLOHEXEN-ALS AND THEIR USE IN PERFUME COMPOSITIONS

(71) Applicants: Benjamin Amorelli, Brielle, NJ (US); Anthony T. Levorse, Jr., Westfield, NJ (US); David Rodriguez, Belleville, NJ (US)

(72) Inventors: Benjamin Amorelli, Brielle, NJ (US); Anthony T. Levorse, Jr., Westfield, NJ (US); David Rodriguez, Belleville, NJ (US)

(73) Assignee: INTERNATIONAL FLAVORS & FRAGRANCES INC. NY (US)

(*) Notice: Subject to any disclaimer, the term of this patent is extended or adjusted under 35 U.S.C. 154(b) by 0 days.

(21) Appl. No.: 14/812,590

(22) Filed: Jul. 29, 2015

(51) Int. Cl.
*A61K 8/18* (2006.01)
*C11B 9/00* (2006.01)
*C07C 47/225* (2006.01)

(52) U.S. Cl.
CPC ........... *C11B 9/0034* (2013.01); *C07C 47/225* (2013.01)

(58) Field of Classification Search
None
See application file for complete search history.

(56) References Cited

U.S. PATENT DOCUMENTS

2005/0101498 A1* 5/2005 Marty .................... C07C 45/29
510/106

* cited by examiner

*Primary Examiner* — Ling Choi
*Assistant Examiner* — Jessica E Whiteley
(74) *Attorney, Agent, or Firm* — Martin Zhang; XuFan Tseng; Elizabeth M. Stover

(57) ABSTRACT

The present invention relates to novel dimethylcyclohexen-als and the incorporation and use thereof as fragrance materials.

12 Claims, No Drawings

DIMETHYLCYCLOHEXEN-ALS AND THEIR USE IN PERFUME COMPOSITIONS

FIELD OF THE INVENTION

The present invention relates to novel dimethylcyclohexen-als and the incorporation and use thereof as fragrance materials.

BACKGROUND OF THE INVENTION

There is an ongoing need in the fragrance industry to provide chemicals with strong odors so that less fragrance is needed to accomplish the desired odor effect. This, therefore, gives perfumers and other persons the freedom to create new fragrances for perfumes, colognes and personal care products without the limitation of cost. In addition to odor strength, practical considerations such as the scale of synthesis operation may also determine the applicability of identified fragrance molecules in commercial use. However, whether the production of a given fragrance molecule can be carried out at a commercial scale is sometimes unpredictable. For these reasons, continuous effort has been made in fragrance industry to investigate and develop economical processes for making fragrance molecules that possess high strength.

One skilled person recognizes and appreciates the combinations of existing fragrance ingredients that possess superior effect when compared to individual ingredients. Such combinations are considered unexpected and inventive (See, for example, U.S. Pat. No. 7,767,640 and U.S. Pat. No. 7,846,886).

SUMMARY OF THE INVENTION

The present invention provides novel chemicals and their unexpected advantageous use in improving, enhancing or modifying the fragrance of perfumes, colognes, toilet waters, cosmetic products, personal care products, fabric care products, cleaning products, air fresheners, and the like.

One embodiment of the present invention is directed to novel dimethylcyclohexen-als represented by the following formula:

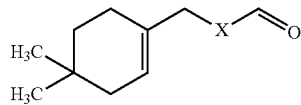

Formula I wherein X represents a linear or branched $C_2$ alkyl group.

Another embodiment of the present invention is directed to the use of the compounds provided above as fragrance materials in perfumes, colognes, toilet waters, personal products, fabric care products, and the like.

Another embodiment of the present invention is directed to a fragrance composition comprising the compounds provided above.

Another embodiment of the present invention is directed to a fragrance product comprising the compounds provided above.

Another embodiment of the present invention is directed to a method of improving, enhancing or modifying a fragrance formulation by incorporating an olfactory acceptable amount of the compounds provided above.

These and other embodiments of the present invention will be apparent by reading the following specification.

DETAILED DESCRIPTION OF THE INVENTION

The dimethylcyclohexen-als of the present invention may be further represented by the following structures:

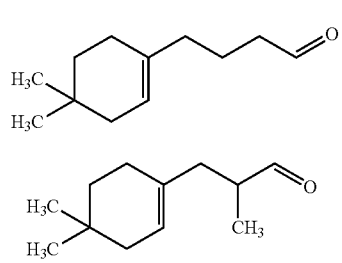

Those with the skill in the art will appreciate that

Formula II is 4-(4,4-dimethyl-cyclohex-1-enyl)-butyraldehyde; and

Formula III is 3-(4,4-dimethyl-cyclohex-1-enyl)-2-methyl-propionaldehyde.

The present invention also relates to a mixture of Formula II and Formula III.

The present invention further relates to a mixture of Formula II and Formula III with a weight ratio of about 4 or lower.

The compounds of the present invention were prepared with 4,4-dimethyl-cyclohexanone according to the following reaction scheme, the details of which are specified in the Examples. Materials and catalysts were purchased from Aldrich Chemical Company unless noted otherwise.

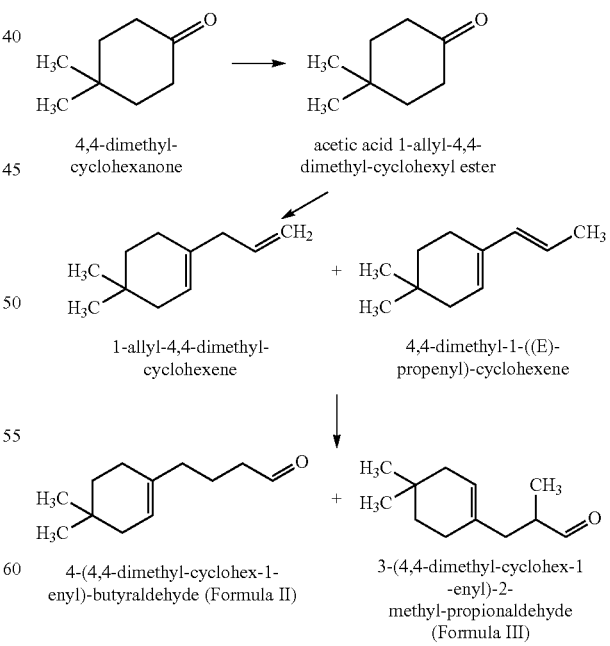

Those with skill in the art will recognize that the isomeric products obtained as described above can be further separated using techniques known to those with skill in the art.

Suitable techniques include, for example, distillation and chromatography such as high performance liquid chromatography, referred to as HPLC, particularly silica gel chromatograph, and gas chromatography trapping known as GC trapping. Yet, commercial products are mostly offered as isomeric mixtures.

Specific ratios of 4-(4,4-dimethyl-cyclohex-1-enyl)-butyraldehyde (Formula II) and 3-(4,4-dimethyl-cyclohex-1-enyl)-2-methyl-propionaldehyde (Formula III) were also obtained.

It has been surprisingly and unexpectedly found that there exist criticality to the mixing ratios of Formula II and Formula III. Specifically, only a dimethylcyclohexen-al mixture containing Formula II and Formula III with a weight ratio of about 4 or lower has been found to possess desirable and useful fragrance properties of high strength while a mixing ratio outside the specified ranges will cause off-notes and render the dimethylcyclohexen-al mixture unsuitable for fragrance use. Thus, the present invention also relates to the surprising and unexpected discovery of the criticality of the mixing ratios in the dimethylcyclohexen-al mixture.

Complexity of odor notes refers to the presence of multiple and/or mixed but defined odors rather than a single note or a few easily identifiable notes. High levels of complexity are also assigned to compounds that possess ambiguous and somehow hard-to-define notes because of direct contribution or the many olfactive combinations of odors produced. Fragrance materials of high level complexity are considered having unusual and high quality.

The use of the dimethylcyclohexen-al mixture of the present invention is widely applicable in current perfumery products, including the preparation of perfumes and colognes, the perfuming of personal care products such as soaps, shower gels, and hair care products, fabric care products, air fresheners, and cosmetic preparations. The present invention can also be used to perfume cleaning agents, such as, but not limited to detergents, dishwashing materials, scrubbing compositions, window cleaners and the like.

In these preparations, the dimethylcyclohexen-al mixture of the present invention can be used alone or in combination with other perfuming compositions, solvents, adjuvants and the like. The nature and variety of the other ingredients that can also be employed are known to those with skill in the art. Many types of fragrances can be employed in the present invention, the only limitation being the compatibility with the other components being employed. Suitable fragrances include but are not limited to fruits such as almond, apple, cherry, grape, pear, pineapple, orange, strawberry, raspberry; musk, flower scents such as lavender-like, rose-like, iris-like, carnation-like. Other pleasant scents include herbal and woodland scents derived from pine, spruce and other forest smells. Fragrances may also be derived from various oils, such as essential oils, or from plant materials such as peppermint, spearmint and the like.

A list of suitable fragrances is provided in U.S. Pat. No. 4,534,891, the contents of which are incorporated by reference as if set forth in its entirety. Another source of suitable fragrances is found in *Perfumes, Cosmetics and Soaps*, Second Edition, edited by W. A. Poucher, 1959. Among the fragrances provided in this treatise are acacia, cassie, chypre, cyclamen, fern, gardenia, hawthorn, heliotrope, honeysuckle, hyacinth, jasmine, lilac, lily, magnolia, mimosa, narcissus, freshly-cut hay, orange blossom, orchid, reseda, sweet pea, trefle, tuberose, vanilla, violet, wallflower, and the like.

The dimethylcyclohexen-al mixture of the present invention can be used in combination with a complementary fragrance compound. The term "complementary fragrance compound" as used herein is defined as a fragrance compound selected from the group consisting of 2-[(4-methylphenyl)methylene]-heptanal (Acalea), iso-amyl oxyacetic acid allylester (Allyl Amyl Glycolate), (3,3-dimethylcyclohexyl) ethyl ethyl propane-1,3-dioate (Applelide), (E/Z)-1-ethoxy-1-decene (Arctical), 2-ethyl-4-(2,2,3-trimethyl-3-cyclo-penten-1-yl)-2-buten-1-ol (Bacdanol), 2-methyl-3-[(1,7,7-trimethylbicyclo[2.2.1]hept-2-yl)oxy]exo-1-propanol (Bornafix), 1,2,3,5,6,7-hexahydro-1,1,2,3,3-pentamethyl-4H-inden-4-one (Cashmeran), trimethylcyclopentenylmethyloxabicyclooctane (Cassiffix), 1,1-dimethoxy-3,7-dimethyl-2,6-octadiene (Citral DMA), 3,7-dimethyl-6-octen-1-ol (Citronellol), 3A,4,5,6,7,7A-hexahydro-4,7-methano-1H-inden-5/6-yl acetate (Cyclacet), 3A,4,5,6,7,7A-hexahydro-4,7-methano-1H-inden-5/6-yl propinoate (Cyclaprop), 3A,4,5,6,7,7A-hexahydro-4,7-methano-1G-inden-5/6-yl butyrate (Cyclobutanate), 1-(2,6,6-trimethyl-3-cyclohexen-1-yl)-2-buten-1-one (Delta Damascone), 3-(4-ethylphenyl)-2,2-dimethyl propanenitrile (Fleuranil), 3-(O/P-ethylphenyl) 2,2-dimethyl propionaldehyde (Floralozone), tetrahydro-4-methyl-2-(2-methylpropyl)-2H-pyran-4-ol (Floriffol), 1,3,4,6,7,8-hexahydro-4,6,6,7,8,8-hexamethylcyclopenta-gamma-2-benzopyran (Galaxolide), 1-(5,5-dimethyl-1-cyclohexen-1-yl)pent-4-en-1-one (Galbascone), E/Z-3,7-dimethyl-2,6-octadien-1-yl acetate (Geranyl Acetate), -methyl-1,3-benzodioxole-5-propanal (Helional), 1-(2,6,6-trimethyl-2-cyclohexen-1-yl)-1,6-heptadien-3-one (Hexalon), (Z)-3-hexenyl-2-hydroxybenzoate (Hexenyl Salicylate, CIS-3), 4-(2,6,6-trimethyl-2-cyclohexen-1-yl)-3-buten-2-one (Ionone α), 1-(1,2,3,4,5,6,7,8-octahydro-2,3,8,8-tetramethyl-2-naphthalenyl)-ethan-1-one (Iso E Super), methyl 3-oxo-2-pentylcyclopentaneacetate (Kharismal), 2,2,4-trimethyl-4-phenyl-butanenitrile (Khusinil), 3,4,5,6,6-pentamethylhept-3-en-2-one (Koavone), 3/4-(4-hydroxy-4-methyl-pentyl) cyclohexene-1-carboxaldehyde (Lyral), 3-methyl-4-(2,6,6-trimethyl-2-cyclohexen-1-yl)-3-buten-2-one (Methyl Ionone γ), 1-(2,6,6-trimethyl-2-cyclohexen-1-yl) pent-1-en-3-one (Methyl Ionone α Extra, Methyl Ionone N), 3-methyl-4-phenylbutan-2-ol (Muguesia), cyclopentadec-4-en-1-one (Musk Z4), 3,3,4,5,5-pentamethyl-11,13-dioxatricyclo[7.4.0.0<2,6>]tridec-2 (6)-ene (Nebulone), 3,7-dimethyl-2,6-octadien-1-yl acetate (Neryl Acetate), 3,7-dimethyl-1,3,6-octatriene (Ocimene), ortho-tolylethanol (Peomosa), 3-methyl-5-phenylpentanol (Phenoxanol), 1-methyl-4-(4-methyl-3-pentenyl) cyclohex-3-ene-1-carboxaldehyde (Precyclemone B), 4-methyl-8-methylene-2-adamantanol (Prismantol), 2-ethyl-4-(2,2,3-trimethyl-3-cyclopenten-1-yl)-2-buten-1-ol (Sanjinol), 2-methyl-4-(2,2,3-trimethyl-3-cyclopenten-1-yl)-2-buten-1-ol (Santaliff), Terpineol, 2,4-dimethyl-3-cyclohexene-1-carboxaldehyde (Triplal), decahydro-2,6,6,7,8,8-hexamethyl-2H-indeno[4,5-B]furan (Trisamber), 2-tert-butylcyclohexyl acetate (Verdox), 4-tert-butylcyclohexyl acetate (Vertenex), acetyl cedrene (Vertofix), 3,6/4,6-dimethylcyclohex-3-ene-1-carboxaldehyde (Vertoliff), and (3Z)-1-[(2-methyl-2-propenyl) oxy]-3-hexene (Vivaldie).

The terms "fragrance formulation", "fragrance composition", and "perfume composition" mean the same and refer to a consumer composition that is a mixture of compounds including, for example, alcohols, aldehydes, ketones, esters, ethers, lactones, nitriles, natural oils, synthetic oils, and mercaptans, which are admixed so that the combined odors of the individual components produce a pleasant or desired fragrance. The fragrance formulation of the present invention is a consumer composition comprising the dimethylcyclohexen-als of the present invention. The fragrance formulation of the present invention comprises the dimethylcyclohexen-als of the present invention and further a complementary fragrance compound as defined above.

The term "fragrance product" means a consumer product that adds a fragrance or masks a malodor. Fragrance products may include, for example, perfumes, colognes, personal care products such as soaps, shower gels, and hair care products, fabric products, air fresheners, cosmetic preparations, and perfume cleaning agents such as detergents, dishwashing materials, scrubbing compositions, and window cleaners. The fragrance product of the present invention is a consumer product that contains the dimethylcyclohexen-als of the present invention. The fragrance product of the present invention contains the dimethylcyclohexen-als of the present invention and further a complementary fragrance compound as defined above.

The term "improving" in the phrase "improving, enhancing or modifying a fragrance formulation" is understood to mean raising the fragrance formulation to a more desirable character. The term "enhancing" is understood to mean making the fragrance formulation greater in effectiveness or providing the fragrance formulation with an improved character. The term "modifying" is understood to mean providing the fragrance formulation with a change in character.

Olfactory acceptable amount is understood to mean the amount of compound in perfume compositions the individual component will contribute to its particular olfactory characteristics, but the olfactory effect of the perfume composition will be the sum of the effects of each of the perfumes or fragrance ingredients. Thus the dimethylcyclohexen-als of the invention can be used to alter the aroma characteristics of the perfume composition, or by modifying the olfactory reaction contributed by another ingredient in the composition. The amount will vary depending on many factors including other ingredients, their relative amounts and the effect that is desired.

The amount of the dimethylcyclohexen-als of the present invention employed in a fragrance formulation varies from about 0.005 to about 70 weight percent, preferably from 0.005 to about 50 weight percent, more preferably from about 0.5 to about 25 weight percent, and even more preferably from about 1 to about 10 weight percent. Those with skill in the art will be able to employ the desired amount to provide desired fragrance effect and intensity. In addition to the dimethylcyclohexen-als of the present invention, other materials can also be used in conjunction with the fragrance formulation. Well known materials such as surfactants, emulsifiers, polymers to encapsulate the fragrance can also be employed without departing from the scope of the present invention.

When used in a fragrance formulation, these ingredients provide aldehydic, muguet, fruity and fresh notes to make the fragrance formulation more desirable and noticeable, and add the perception of value. The odor qualities found in this material assist in beautifying and enhancing the finished accord as well as improving the performance of the other materials in the fragrance.

In addition, the compounds of the present invention are also surprisingly found to provide superior ingredient performance and possess unexpected advantages in malodor counteracting applications such as body perspiration, environmental odor such as mold and mildew, bathroom, and etc. The compounds of the present invention substantially eliminate the perception of malodors and/or prevent the formation of such malodors, thus, can be utilized with a vast number of functional products.

Examples of the functional products are provided herein to illustrate the various aspects of the present invention. However, they do not intend to limit the scope of the present invention. The functional products may include, for example, a conventional room freshener (or deodorant) composition such as room freshener sprays, an aerosol or other spray, fragrance diffusers, a wick or other liquid system, or a solid, for instance candles or a wax base as in pomanders and plastics, powders as in sachets or dry sprays or gels, as in solid gel sticks, clothes deodorants as applied by washing machine applications such as in detergents, powders, liquids, whiteners or fabric softeners, fabric refreshers, linen sprays, closet blocks, closet aerosol sprays, or clothes storage areas or in dry cleaning to overcome residual solvent notes on clothes, bathroom accessories such as paper towels, bathroom tissues, sanitary napkins, towellets, disposable wash cloths, disposable diapers, and diaper pail deodorants, cleansers such as disinfectants and toilet bowl cleaners, cosmetic products such as antiperspirant and deodorants, general body deodorants in the form of powders, aerosols, liquids or solid, or hair care products such as hair sprays, conditioners, rinses, hair colors and dyes, permanent waves, depilatories, hair straighteners, hair groom applications such as pomade, creams and lotions, medicated hair care products containing such ingredients as selenium sulphide, coal tar or salicylates, or shampoos, or foot care products such as foot powders, liquids or colognes, after shaves and body lotions, or soaps and synthetic detergents such as bars, liquids, foams or powders, odor control such as during manufacturing processes, such as in the textile finishing industry and the printing industry (inks and paper), effluent control such as in processes involved in pulping, stock yard and meat processings, sewage treatment, garbage bags, or garbage disposal, or in product odor control as in textile finished goods, rubber finished goods or car fresheners, agricultural and pet care products such as dog and hen house effluents and domestic animal and pet care products such as deodorants, shampoo or cleaning agents, or animal litter material and in large scale closed air systems such as auditoria, and subways and transport systems.

Thus, it will be seen that the composition of the invention is usually one in which the malodor counteractant is present together with a carrier by means of which or from which the malodor counteractant can be introduced into air space wherein the malodor is present, or a substrate on which the malodor has deposited. For example, the carrier can be an aerosol propellant such as a chlorofluoro-methane, or a solid such as a wax, plastics material, rubber, inert powder or gel. In a wick-type air freshener, the carrier is a substantially odorless liquid of low volatility. In several applications, a composition of the invention contains a surface active agent or a disinfectant, while in others, the malodor counteractant is present on a fibrous substrate. In many compositions of the invention there is also present a fragrance component which imparts a fragrance to the composition. The fragrances stated above can all be employed.

Malodor counteracting effective amount is understood to mean the amount of the inventive malodor counteractant employed in an air space or a substrate such as a functional product that is organoleptically effective to abate a given malodor while reducing the combined intensity of the odor level, wherein the given malodor is present in air space or has deposited on a substrate. The exact amount of malodor counteractant agent employed may vary depending upon the type of malodor counteractant, the type of the carrier employed, and the level of malodor counteractancy desired. In general, the amount of malodor counteractant agent present is the ordinary dosage required to obtain the desired result. Such dosage is known to the skilled practitioner in the art. In a preferred embodiment, when used in conjunction with malodorous solid or liquid functional products, e.g., soap and detergent, the compounds of the present invention may be present in an amount ranging from about 0.005 to about 50 weight percent, preferably from about 0.01 to about 20 weight percent, more preferably from about 0.05 to about 10 weight percent and even more preferably from about 0.1 to about 5 weight percent. When used in an air space that is in conjunction with malodorous gaseous functional products, the compounds of the present invention may be present in an amount ranging from about 0.2 mg to about 2 g per cubic meter of air, more preferably from about 0.4 mg to about 0.8 g per cubic meter of air, more preferably from about 2 mg to about 0.4 g per cubic meter of air and even more preferably from about 4 mg to about 0.2 g per cubic meter of air.

The following are provided as specific embodiments of the present invention. Other modifications of this invention will be readily apparent to those skilled in the art. Such modifications are understood to be within the scope of this invention. The chemical materials used in the preparation of the compounds of the present invention are commercially available from Aldrich Chemical Company. As used herein all percentages are weight percent unless otherwise noted, ppm is understood to stand for parts per million, mol is understood to be mole, mmol is understood to be millimole, L is understood to be liter, mL is understood to be milliliter and psi is understood to be pound-force per square inch. IFF as used in the examples is understood to mean International Flavors & Fragrances Inc., New York, N.Y., USA.

EXAMPLE I

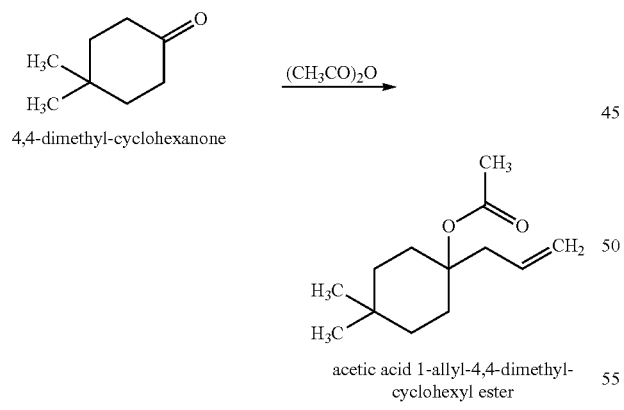

Preparation of Acetic Acid 1-Allyl-4,4-dimethyl-cyclohexyl Ester

A solution of 4,4-dimethyl-cyclohexanone (202 g, 1.60 mol) in 100 mL of toluene was added dropwise to a solution of allylmagnesium chloride (CH$_2$=CHCH$_2$MgCl) (2 M, 800 mL) in tetrahydrofuran (THF) while the reaction temperature was maintained at 0-15° C. After the addition was completed, the reaction mixture was allowed to warm to room temperature and aged for 1 hour. Acetic anhydride ((CH$_3$CO)$_2$O) (204 g, 2.0 mol) was fed via a dropping funnel over ~5 minutes. The mixture was carefully allowed to warm to reflux during the feeding while the reaction exothermed. Upon the completion of the feeding, the viscous mixture was diluted with ethyl acetate (CH$_3$COOCH$_2$CH$_3$) until it became completely homogeneous. The mixture was then quenched into aqueous acetic acid (CH$_3$COOH) (200 mL) in ice water/brine (500 mL). The organic layer was washed with aqueous sodium carbonate (Na$_2$CO3) until slightly basic, dried over sodium sulfate (Na$_2$SO$_4$) and further distilled (80° C., 2.32 torr) to provide acetic acid 1-allyl-4,4-dimethyl-cyclohexyl ester (315 g).

$^1$H NMR (CDCl$_3$, 500 MHz): 5.72-5.80 ppm (m, 1H), 5.04-5.08 ppm (m, 2H), 2.65 ppm (d, 2H, J=7.40 Hz), 2.08-2.12 ppm (m, 2H), 1.99 ppm (s, 3H), 1.46-1.54 ppm (m, 2H), 1.34-1.42 ppm (m, 2H), 1.18-1.24 ppm (m, 2H), 0.93 ppm (s, 3H), 0.89 ppm (s, 3H)

EXAMPLE II

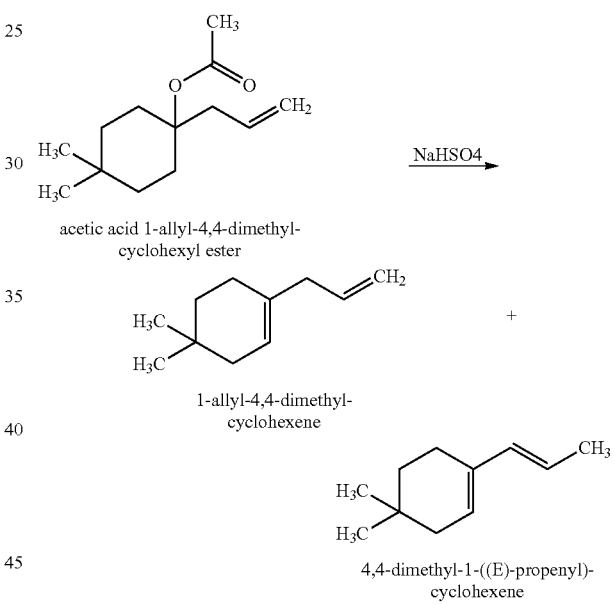

Preparation of 1-Allyl-4,4-dimethyl-cyclohexene and 4,4-Dimethyl-1-((E)-propenyl)-cyclohexene A solution of 1-allyl-4,4-dimethyl-cyclohexyl ester (391 g, 1.86 mol, obtained in EXAMPLE I) and sodium hydrogen sulfate (NaHSO$_4$) (22.3 g, 0.186 mol) in 500 mL of toluene was heated at reflux for 6 hours. The reaction mixture was washed with aqueous sodium carbonate, dried over sodium sulfate and then distilled (81° C., 30 torr) to provide 1-allyl-4,4-dimethyl-cyclohexene (173 g) and 4,4-dimethyl-1((E)-propenyl)-cyclohexene (87 g).

1-Allyl-4,4-dimethyl-cyclohexene $^1$H NMR (CDCl$_3$, 500 MHz): 5.75-5.85 ppm (m, 1H), 5.32-5.36 ppm (m, 1H), 4.97-5.07 ppm (m, 2H), 2.68 ppm (d, 2H, J=6.55 Hz), 1.92-1.95 ppm (m, 2H), 1.77-1.80 ppm (m, 2H), 1.35 ppm (t, 2H, J=6.35 Hz), 0.89 ppm (s, 6H)

4,4-Dimethyl-1-((E)-propenyl)-cyclohexene $^1$H NMR (CDCl$_3$, 500 MHz): 6.03 ppm (d, 1H, J=15.56 Hz), 5.45-5.60 ppm (m, 2H), 2.05-2.15 (m, 2H), 1.83-1.89 ppm (m, 2H), 1.73 ppm (d, 3H, J=6.35 Hz), 1.39 ppm (t, 2H, J=6.48 Hz), 0.88 ppm (s, 6H)

EXAMPLE III

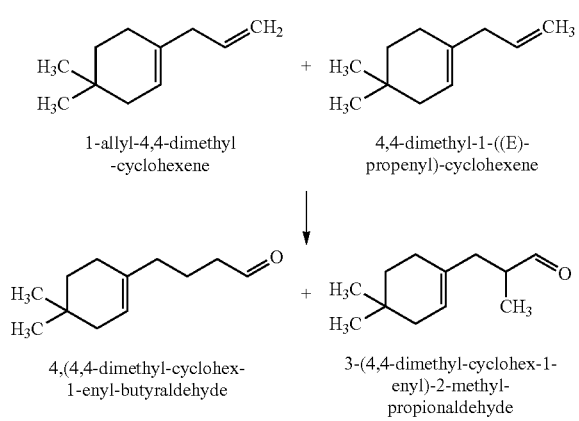

1-allyl-4,4-dimethyl-cyclohexene 4,4-dimethyl-1-((E)-propenyl)-cyclohexene 4,(4,4-dimethyl-cyclohex-1-enyl-butyraldehyde 3-(4,4-dimethyl-cyclohex-1-enyl)-2-methyl-propionaldehyde Preparation of 4-(4,4-Dimethyl-cyclohex-1-enyl)-butyraldehyde (Formula II) and 3-(4,4-Dimethyl-cyclohex-1-enyl)-2-methyl-propionaldehyde (Formula III)

A mixture containing about 67% of 1-allyl-4,4-dimethyl-cyclohexene and about 33% of 4,4-dimethyl-1-((E)-propenyl)-cyclohexene (260 g, 1.73 mol, obtained in EXAMPLE II) and hydridocarbonyl-tris(triphenylphosphine)-rhodium (I) (RhH(CO)(PPh$_3$)$_3$) (1.2 g, RH-42) were heated at 80° C. in a pressure vessel with syngas (1:1 H$_2$/CO) at 300 psi for 2 hours. The resulting mixture was distilled (93° C., 5.67 torr) to provide a mixture of 4-(4,4-dimethyl-cyclohex-1-enyl)-butyraldehyde (Formula II) and 3-(4,4-dimethyl-cyclohex-1-enyl)-2-methyl-propionaldehyde (Formula III) with a weight ratio of 7:3 (188 g).

4-(4,4-Dimethyl-cyclohex-1-enyl)-butyraldehyde (Formula II)

$^1$H NMR (CDCl$_3$, 400 MHz): 9.76 ppm (t, 1H, J=1.76 Hz), 5.33 ppm (m, 1H), 2.39 ppm (t, 2H, J=7.35 Hz, of d, J=1.40 Hz), 1.86-2.02 ppm (m, 4H), 1.70-1.79 ppm (m, 4H), 1.35 ppm (t, 2H, J=6.42 Hz), 0.89 ppm (s, 6H)

Formula II was described as having muguet, aldehydic, green and waxy notes.

3-(4,4-Dimethyl-cyclohex-1-enyl)-2-methyl-propionaldehyde (Formula III)

$^1$H NMR (CDCl$_3$, 500 MHz): 9.62 ppm (d, 1H, J=1.80 Hz), 5.38 (m, 1H), 2.47-2.55 ppm (m, 1H), 2.34-2.40 (m, 1H), 1.71-2.02 ppm (m, 5H), 1.33-1.38 ppm (m, 2H), 1.04 ppm (d, 3H, J=6.90 Hz), 0.89 ppm (s, 6H)

Formula III was described as having watery, melon-like, slight citrus and muguet notes.

EXAMPLE III

Evaluation of 4-(4,4-Dimethyl-cyclohex-1-enyl)-butyraldehyde (Formula II) and 3-(4,4-Dimethyl-cyclohex-1-enyl)-2-methyl-propionaldehyde (Formula III) Mixtures with Different Ratios The following mixture samples were prepared and evaluated for odor properties using (i) odor strength of 0 to 10, where 0=none, 1=very weak, 5=moderate, 10=extremely strong; and (ii) level of complexity, where 0=none, 1=very low, 5=moderate, 10=extremely high. Averaged scores are reported in the following:

| Sample | Weight Ratio (Formula II:III) | Odor Profile | Strength | Complexity |
|---|---|---|---|---|
| 1 | 1 | Fresh, watery and fruity with powerful aldehydic green top note. An ozonic note added freshness. | 9 | 9 |
| 2 | 2 | Fresh, green, aldehydic with soft and appealing impression. An ozonic note provided freshness and supported the green aspect. A watery character added additional dimension and supported floral complexity. | 9.5 | 9.5 |
| 3 | 2.5 | Powerful aldehydic with bright, crispy, fruity and fresh top notes and diffusive character. An ozonic note added complexity and elegance. An orris note provided depth and body. An aldehydic muguet note enhanced complexity and provided additional differentiation from other molecules in this odor region. | 10 | 9.5 |
| 4 | 4 | Fresh, aldehydic, clean and crispy top notes with muguet, watery and diffusive characters. | 8.5 | 8.5 |
| 5 | 6 | Less appealing due to the loss of strength and crispy green quality. Top notes were solvent-like and slightly burnt. | 5 | 5 |
| 6 | 9 | Aldehydic and sweet top notes but weak. Overall body appeared thin with a burning character. | 5 | 5 |

The above evaluation yielded unexpected finding, samples 1-4 were surprisingly superior to samples 5 and 6. There was criticality to the mixing ratios of 4-(4,4-dimethyl-cyclohex-1-enyl)-butyraldehyde (Formula II) and 3-(4,4-dimethyl-cyclohex-1-enyl)-2-methyl-propionaldehyde (Formula III). Specifically, only a mixture containing Formula II and Formula III with a weight ratio of about 4 or lower was found to possess desirable fragrance properties of high strength while a mixing ratio outside the defined ranges caused off-notes which rendered the dimethylcyclohexen-al mixture unsuitable for fragrance use. Thus, the present invention has also made surprising and unexpected discovery of the criticality of the mixing ratios in a dimethylcyclohexen-al mixture.

What is claimed is:
1. A mixture of 4-(4,4-dimethyl-cyclohex-1-enyl)-butyraldehyde and 3-(4,4-dimethyl-cyclohex-1-enyl)-2-methyl-propionaldehyde.
2. The mixture of claim 1, wherein 4-(4,4-dimethyl-cyclohex-1-enyl)-butyraldehyde and 3-(4,4-dimethyl-cyclohex-1-enyl)-2-methyl-propionaldehyde have a weight ratio of about 4 or lower.

3. A fragrance formulation containing an olfactory acceptable amount of a mixture of 4-(4,4-dimethyl-cyclohex-1-enyl)-butyraldehyde and 3-(4,4-dimethyl-cyclohex-1-enyl)-2-methyl-propionaldehyde.

4. The fragrance formulation of claim 3, wherein 4-(4,4-dimethyl-cyclohex-1-enyl)-butyraldehyde and 3-(4,4-dimethyl-cyclohex-1-enyl)-2-methyl-propionaldehyde have a weight ratio of about 4 or lower.

5. The fragrance formulation of claim 3, wherein the olfactory acceptable amount is from about 0.005 to about 50 weight percent of the fragrance formulation.

6. The fragrance formulation of claim 3, wherein the olfactory acceptable amount is from about 0.1 to about 25 weight percent of the fragrance formulation.

7. The fragrance formulation of claim 3, wherein the olfactory acceptable amount is from about 0.5 to about 10 weight percent of the fragrance formulation.

8. A method of improving, enhancing or modifying a fragrance formulation through the addition of an olfactory acceptable amount of a mixture of 4-(4,4-dimethyl-cyclohex-1-enyl)-butyraldehyde and 3-(4,4-dimethyl-cyclohex-1-enyl)-2-methyl-propionaldehyde.

9. The method of claim 8, wherein 4-(4,4-dimethyl-cyclohex-1-enyl)-butyraldehyde and 3-(4,4-dimethyl-cyclohex-1-enyl)-2-methyl-propionaldehyde have a weight ratio of about 4 or lower.

10. A fragrance product containing an olfactory acceptable amount of a mixture of 4-(4,4-dimethyl-cyclohex-1-enyl)-butyraldehyde and 3-(4,4-dimethyl-cyclohex-1-enyl)-2-methyl-propionaldehyde.

11. The fragrance product of claim 10, wherein 4-(4,4-dimethyl-cyclohex-1-enyl)-butyraldehyde and 3-(4,4-dimethyl-cyclohex-1-enyl)-2-methyl-propionaldehyde have a weight ratio of about 4 or lower.

12. The fragrance product of claim 10, wherein the fragrance product is selected from the group consisting of a perfume, a cologne, toilet water, a cosmetic product, a personal care product, a fabric care product, a cleaning product and an air freshener.

* * * * *